US006444471B1

(12) United States Patent
Johnson

(10) Patent No.: US 6,444,471 B1
(45) Date of Patent: Sep. 3, 2002

(54) RETICULOCYTE CONTAINING COMPLETE BLOOD CONTROL

(75) Inventor: Alan M. Johnson, New Brighton, MN (US)

(73) Assignee: Research & Diagnostic Systems, Inc., Minneapolis, MN (US)

( * ) Notice: Subject to any disclaimer, the term of this patent is extended or adjusted under 35 U.S.C. 154(b) by 0 days.

(21) Appl. No.: 09/419,991

(22) Filed: Oct. 18, 1999

(51) Int. Cl.$^7$ ............................................... G01N 31/00
(52) U.S. Cl. ............................. 436/10; 436/8; 436/63; 436/176; 435/2; 435/29; 435/810; 422/61; 252/408.1
(58) Field of Search ............................ 436/8, 10, 16, 436/18, 63, 174–177; 435/2, 29, 34, 39, 810; 422/61, 73; 252/408.1

(56) References Cited

U.S. PATENT DOCUMENTS

| | | | |
|---|---|---|---|
| 4,324,686 A | 4/1982 | Mundschenk | |
| 4,338,564 A | 7/1982 | Mundschenk | |
| 4,447,547 A | 5/1984 | Allen et al. | |
| 4,704,364 A | 11/1987 | Carver et al. | 436/10 |
| 4,777,139 A | 10/1988 | Wong et al. | 436/18 |
| 5,320,964 A | 6/1994 | Young et al. | 436/10 |
| 5,380,664 A | 1/1995 | Carver et al. | 436/10 |
| 5,432,089 A | 7/1995 | Ryan et al. | 436/10 |
| 5,733,784 A | 3/1998 | Studholme et al. | 436/63 |
| 5,736,402 A | 4/1998 | Francis et al. | 436/10 |
| 5,858,789 A | 1/1999 | Francis et al. | 436/10 |
| 5,858,790 A | 1/1999 | Kim et al. | 436/16 |
| 5,945,340 A | 8/1999 | Francis et al. | 436/10 |
| 5,994,139 A | * 11/1999 | Jacobs et al. | 436/10 |
| 6,200,500 B1 | 3/2001 | Ryan | 252/408.1 |
| 6,221,668 B1 | 4/2001 | Ryan et al. | 436/8 |

OTHER PUBLICATIONS

Bulova, S. et al., "Template Activity for Globin and Non–Globin Protein Synthesis in Reticulocytes", *The Journal of Biological Chemistry*, vol. 247, No. 10, pp. 3101–3106 (May 25, 1972).
Beutler, E. et al., "The Removal of Leukocytes and Platelets from Whole Blood", *J. Lab. Clin. Med.*, vol. 88, No. 2, pp. 328–333 (Aug. 1976).
Beutler, E. et al., "The Mechanism of Removal of Leukocytes by Cellulose Columns", *Blood Cells*, vol. 12, pp. 57–64 (1986).
Burton, A., "Automation of the Reticulocyte Count", *Clinical Note*, 2 pages (Jan. 1994).
"Body Fluids, Hematology, and Immunology." *The Biology of the Pig*, pp. 254–256, 86–87, Date Unknown.
Couler Cell Control, "Retic–C Coulter® Cell Control" 2 pages (1983).
Davis, B., "Immature Reticulocyte Fraction (IRF): By Any Name, A Useful Clinical Paramter of Erythropoietic Activity", *Laboratory Hematology*, vol. 2, pp. 2–8 (1996).
Davis, B. et al., "Flow Cytometric Reticulocyte Analysis and the Reticulocyte Maturity Index", *Annals New York Academy of Sciences*, pp. 281–291 (Date Unknown).
Howen, B, "Reticulocyte Maturation", *Blood Cells*, vol. 18, pp. 167–186 (1992).
Koepke, J. et al., "Reticulocytes", *Clin. Lab. Haemet*, vol. 8, pp. 169–179 (1986).
Savage, R. et al., "Analytic Inaccuracy and Imprecision in Reticulocyte Counting: A Preliminary Report from the College of American Pathologists Reticulocyte Project", *Blood Cells*, vol. 11, pp 97–112 (1985).
Tsuda, I. et al., "Reticulocytes in Human Preserved Blood as Control Material for Automated Reticulocyte Counters", *Am. J. Clin. Pathol.*, vol. 93, pp. 109–110, (Jan., 1990).
Van Hove, L. et al., "CELL–DYN® 4000 The Next Generation Hematology Analyzer", *Abbott Diagnostics*, (Date Unknown).
Van Hove, L. et al., "CELL–DYN® 4000 Reticulocyte Assay", *Abbott Diagnostics*, (Date Unknown).
"TESTpoint™ Reticulocyte Control/Contrôle Pour Réticulocytes/Retikulozyten–Kontrolle T03–3537M01", *Miles*, 4 pages (Date Unknown).
"Reticulocyte Counting by Flow Cytometry; Proposed Guideline", *National Committee for Clinical Laboratory Standards*, Document H44–P, vol. 13, No. 18, pp. 1–30 (Nov. 1993).
"Discussions in Hematology", *R&D Systems*, vol. 1, No. 2, pp. 1–8, (Winter, 1995).
"RETIC–CHEX® Assay and Instructional Information", *Streck Laboratories, Inc.*, (Apr. 1993).

* cited by examiner

*Primary Examiner*—Maureen M. Wallenhorst
(74) *Attorney, Agent, or Firm*—Fredrikson & Byron, PA

(57) ABSTRACT

A control composition, and method of preparing a control composition, that includes stabilized, maturation-arrested reticulocytes, and a complete blood count base including mature erythrocytes, stabilized white cells and stabilized platelets, or analogs thereof.

17 Claims, 2 Drawing Sheets

RETICULOCYTE CONTAINING COMPLETE BLOOD CONTROL

TECHNICAL FIELD

The present invention relates to the field of hematology, and in particular, to assays for determining the number or presence of the formed elements of blood such as red blood cells, white blood cells, platelets and reticulocytes. More specifically, the invention relates to control compositions used in performing such assays, and to processes for preparing, and methods of using such control compositions.

BACKGROUND OF THE INVENTION

The field of hematology involves the study of blood, including the discrete cell populations that make up the blood and blood forming organs. The ability to reliably and accurately distinguish and count cells is one important tool in this field. Clinical significance can be attributed to abnormal levels, in both relative and absolute terms, of most cell populations.

The study of the dynamics of blood cell production and destruction depends upon the enumeration of new cells being delivered to the circulation per unit time. New immature red blood cells (known as reticulocytes) are easily identified and can be quantified as a percentage of total red blood cells ("RBCs").

A reticulocyte is created during the final stages of erythroid development, resulting from the enucleation of RNA-rich, orthochromatic normoblasts. The feature of reticulocytes most frequently used to distinguish them from mature RBCs is their stainable RNA. Reticulocytes most recently released into blood from the bone marrow compartment contain the highest levels of cellular RNA. As reticulocytes mature, the cells gradually lose RNA, and this biochemical change can be used to determine not only the presence of reticulocytes, but also can serve as an indicator of reticulocyte maturational stages. Within 1 to 2 days from being released from the bone marrow compartment, the reticulocytes lose RNA to a point where the cells become indistinguishable from mature RBCs.

As a result of the foregoing, reticulocytes can be distinguished from mature red blood cells by the presence in reticulocytes of cellular RNA. Other less prevalent methods of identifying reticulocytes involve staining of mitochondria, ribosomes, and other cytoplasmic organelles (with so-called supravital dyes, such as new methylene blue, brilliant cresyl blue, and acridine orange), as well as methods involving recognition of cell surface markers unique to reticulocytes. The reticulocyte percentage is then multiplied by the red cell count in order to provide the number of reticulocytes per microliter.

Reticulocytes require 3 to 4 days to mature into non-stainable red blood cells, with about 2 to 3 days of this period being spent in the bone marrow and about 1 to 2 days being spent in the peripheral blood. The reticulocyte count can be clinically significant, if accurately measured. Levels approaching 3% of the total number of circulating red cells may indicate increased marrow activity, e.g., when blood synthesis is stimulated with erythropoietin. In contrast, levels below about 0.5% can be an indication of bone marrow incompetence. Hence, a reticulocyte count is an effective measure of marrow erythroid output.

Many approaches have been described for determining absolute and/or relative reticulocyte levels. Although such approaches have traditionally been performed manually, automated procedures are being used with increasing frequency. An increasing number of manufacturers of automated cell counting instruments have added the ability to count reticulocytes to their systems. Additionally, some instruments provide the ability to measure the relative maturity of reticulocytes, which is inversely proportional to the amount of stainable matter (e.g., RNA) within the cell. This indicates the relative age of the reticulocyte leaving the bone marrow. Such values may be referred to as the immature reticulocyte fraction ("IRF"), the reticulocyte maturation index ("RMI"), and other such terms commonly used to describe this measurement.

The newest of the cell counting instruments include the reticulocyte count, complete blood count ("CBC"), and the white blood cell ("WBC") differential count. However, current controls for such instruments are separate products (i.e., separate CBC/WBC differential control and separate reticulocyte control) that must be run on these instruments in two distinct steps. In general, a CBC plus differential control critiques the ability of a diagnostic instrument to correctly determine the total white cell count and the percentage of the five major classes of white blood cells (leukocytes) commonly found in circulation which comprise this total, namely, lymphocytes, neutrophils, monocytes, eosinophils, and basophils, as well as total RBCs and platelets in the sample. When using these latest counting instruments, the CBC/WBC differential control is run and recovered values for this control are compared with expected values. Thereafter, the reticulocyte only control is run and recoveries are compared with the expected values.

Thus, the present inventors believe it would be advantageous to provide a single hematology control that allows measurement of the formed elements of blood, including reticulocytes, red blood cells, white blood cells, (and subpopulations thereof) and platelets. Such a unitary control would avoid the necessity of performing separate counts to obtain values for the components of whole blood.

Each reticulocyte counting method relies upon a standardized reticulocyte control to assess the accuracy and reliability of the results. Reticulocyte-only controls have been provided in a number of different forms. Human blood is generally considered a poor source of reticulocytes for controls, because it is typically too low in reticulocyte count to be useful for the preparation of a wide range of control levels.

A control composition known as Retic-C™ is available in three control levels from Beckman/Coulter Corporation (Miami, Fla.). This product includes avian red blood cells as reticulocyte analogues. Avian RBCs are significantly larger than human reticulocytes and, in contrast to reticulocytes, also contain a nucleus. Because these cells are not true reticulocytes, they do not stain in the manner common to reticulocytes. As a result, the composition is limited to use on Coulter automated instruments such as the Coulter STKS™.

Another reticulocyte-only control composition is a reticulocyte analogue product available as the Retic-CHEX™ from Streck Laboratories (Omaha, Nebr.). This control contains a reticulocyte analogue that suffers from poor staining intensity and displays characteristics only somewhat like that of true reticulocytes. Yet other control compositions, both of which are manufactured by Streck Laboratories, include the Test Point™ product (available in 2% and 5% levels for use with Bayer instruments), and a 2% and 5% level control available for instruments manufactured by Sysmex. Both compositions are limited in that they provide only two reticulocyte levels, with the upper level being significantly lower than desired.

The present inventors previously described a reticulocyte-only control composition comprising stabilized, maturation-arrested porcine reticulocytes in a red blood cell base, wherein the red blood cell base comprises mature erythrocytes. The present inventors have also described methods of preparing and methods of using such a reticulocyte control. See U.S. Pat. Nos. 5,858,789 and 5,736,402, and 5,945,340 (all of which are commonly owned by the assignee of the present application, and the disclosure of each is incorporated by reference). Unlike the controls described above, this reticulocyte control contains true reticulocytes, obtained from pigs. By avoiding the use of reticulocyte analogs as described above in connection with other commercially available products, this control provides a more accurate reticulocyte count. As described in the cited patents, mature erythrocytes for the control can be provided from porcine, human, or other mammalian sources.

The above reticulocyte controls provide stand-alone controls that measure the levels of only reticulocytes in a sample. These controls can be used in the reticulocyte step of the two-stage whole blood analysis described above. However, it would be particularly advantageous if a single control were capable of identifying and quantitating the various parameters of a whole blood sample, including total RBC, WBC, platelet and reticulocyte content. Such a whole blood control would more closely resemble a whole blood sample of a patient, which would in turn allow a more complete analysis of a sample.

Previously, reticulocytes had to be measured in a separate mode or by a completely separate analysis, as discussed above. This separate analysis was necessary because the diagnostic instruments were not capable of measuring the CBC/WBC differential as well as reticulocytes in the same sample run. Although such CBC/WBC differential controls typically contained a small amount of residual reticulocytes, such reticulocytes were simply present within the red blood cell source used to prepare the control, and were not intentionally added to the control in a significant amount. Such CBC/WBC differential controls generally contained, at most, 1% or less reticulocytes. In addition, the reticulocyte count and maturation level in such samples were not carefully controlled, making such samples inappropriate for use as reticulocyte controls.

Some currently available reticulocyte controls have significant practical limitations in wide-scale application as whole blood controls. If the control includes cells that simulate reticulocytes and contain a nucleus (e.g., avian RBCs), for example, these cells may adversely affect the total WBC count, and may possibly interfere with the WBC differential of the control. The presence of a nucleus, as well as the size of the reticulocyte component of the control, can interfere with the identification of other nucleated cells in the sample.

There do not appear to be any control compositions available today that provide an optimal combination of stability, true reticulocyte appearance and stain characteristics, and wide utility with most of the presently available assay techniques, that are further incorporated into a complete hematology control matrix which most resembles a patient sample. Hence, there is a need for a control composition providing an optimal combination of these properties, which can be used with semi-automated and automated procedures.

SUMMARY OF THE INVENTION

The present invention provides a control composition comprising a predetermined concentration of stabilized reticulocytes in a complete hematology control matrix. In one embodiment, the complete hematology control matrix comprises a complete blood count base that includes mature erythiocytes (red blood cells), stabilized white blood cells or white blood cell analogs, and stabilized platelets or platelet analogs.

In a preferred embodiment, the reticulocytes are maturation-arrested by treatment with a reticulocyte storage buffer which optimally includes an inhibitor of eucaryotic protein synthesis or metabolism. In this embodiment, the relative maturity of the reticulocytes can be controlled to provide a desired maturity profile within the control. Particularly preferred inhibitors are selected from cycloheximide and rifampicin.

An additional embodiment comprises a ready-to-use kit which includes a number of control compositions wherein one or more of the control compositions include reticulocytes, mature red blood cells, stabilized white blood cells (or analogs thereof), and stabilized platelets (or analogs thereof). In one preferred version of this embodiment, the reticulocytes are provided at concentrations from about 0.5% to about 25%. More preferably, reticulocytes are provided at concentrations from about 0.5% to about 15%. In an optimal embodiment, the reticulocytes are provided at concentrations from about 1% to about 12%.

The invention also encompasses a method of preparing a control composition that includes the steps of harvesting an enriched population of reticulocytes; treating the reticulocytes with a suitable medium to arrest further maturation; stabilizing the harvested, arrested reticulocytes; and preparing a control composition that includes a pre-determined concentration of these stabilized, maturation-arrested reticulocytes, RBCs, WBCs (or analogs thereof), and platelets (or analogs thereof). The process of harvesting reticulocytes can involve a differential sedimentation process described in more detail below. Optimally, the treatment of the reticulocytes with a suitable medium generates a maturity profile, so that the relative maturity of the reticulocytes to be used in the control can be controlled.

The resulting control composition provides an optimal combination of such properties as true reticulocyte appearance and stain characteristics; stability; uniformity; and wide utility as a control with most, if not all, presently available assay techniques. Additionally, the present invention provides a unitary control that more closely resembles a patient sample and allows measurement of reticulocyte levels and relative maturity of reticulocytes.

According to the present invention, the addition of the reticulocyte count to the CBC/WBC differential yields a more complete assessment of erythropoietic activity. A CBC/WBC differential plus reticulocyte control provides a hematology control that more closely simulates a human whole blood sample. Further, the analysis of the relative RNA content of circulating reticulocytes yields additional information regarding the rate of erythrocyte regeneration. The ability to reproducibly control the maturity of the reticulocyte component of the control also enables assessment of the analyzer's ability to detect recently synthesized erythroid cells entering the circulation. The present invention can be used with a variety of analytical methods, for example, semi-automated and automated methods to analyze whole blood samples in a single step.

DETAILED DESCRIPTION

Figure 1:
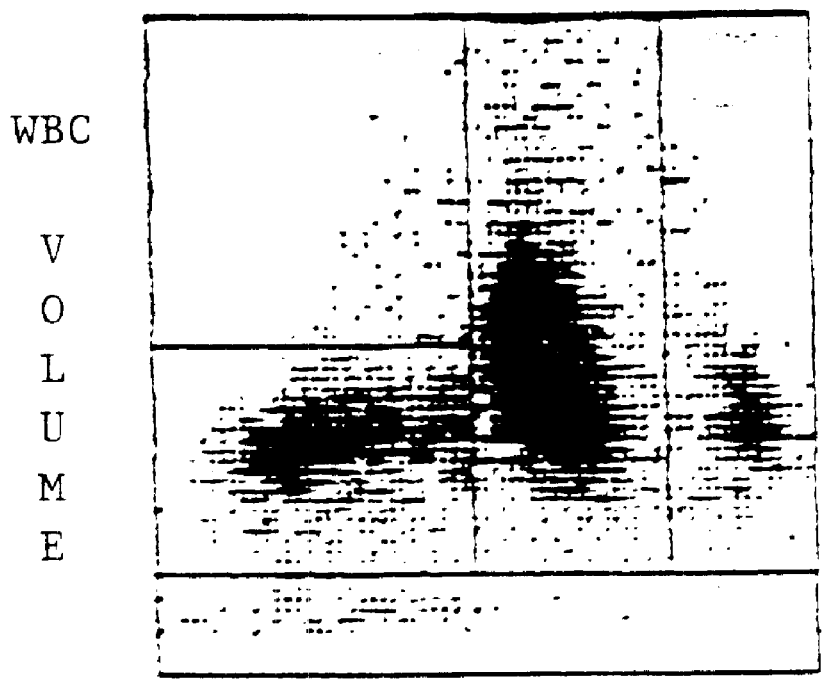
FIG. 1 is a WBC cytogram of R&D Systems CBC-5D™ Hematology Control run on a Coulter STKS™ light scatter based analyzer.

As used herein, "red cells" refers to peripheral blood cells of the erthyropoieitic lineage. A high concentration of hemoglobin (approximately 99% of the protein weight of erythrocytes) gives the red cells their color. Red cells can include nucleated red cells, reticulocytes, and mature red blood cells. "Red blood cells," or "RBCs," will refer to a subpopulation of red cells that comprises mature red cells only.

The word "arrest," and inflections thereof, refers to reticulocytes that are substantially inhibited, either reversibly or irreversibly, from undergoing further natural maturation in a manner that would diminish their utility as a reticulocyte control. Typically, maturation of reticulocytes corresponds with a loss of distinctive cellular material (e.g., RNA) that is stainable using conventional techniques, e.g., chromogenic or fluorogenic supravital dyes.

The word "stabilize," or "stabilized" and inflections thereof, as used herein, refers to cells (e.g., RBC, WBC, platelets, and/or reticulocytes) that are provided in a form that allows the cells to be stored and used in a manner that does not unduly diminish their utility as a hematology control. Generally, stabilization involves the preparation of a suspension containing such cells in combination with one or more ingredients that are useful as preservatives. For example, control compositions are provided in a form having 2-month, 3-month, or longer shelf stability when stored under refrigeration.

As used in this application the term "control" refers to a suspension of cells or cell-like substances that is analyzed by diagnostic instruments and is intended to resemble a patient blood sample when analyzed. Such controls are provided to measure the consistency and/or accuracy of diagnostic instruments and/or methods of analysis of patient samples. Thus, such controls are manufactured to provide expected values for the various blood components. These expected values are assigned by the control manufacturer and are obtained with instruments that are more reliably maintained and calibrated than is possible in routine clinical labs. Such controls are preferably stable, so that they allow the user to establish whether the diagnostic instrument performs consistently and whether it reports the expected values. The control thus serves an important quality control function in clinical laboratories, offering assurance that the instruments and technicians are working properly and other variables are maintained in acceptable limits. Such controls can highlight when instrument service or technician training is necessary, for example.

Compositions of the present invention can be prepared from whole blood obtained from porcine, human, bovine, or other suitable mammalian sources. For example, the reticulocyte component of the control can be prepared from whole porcine blood, or fractions thereof, according to any suitable preparative procedure. The following is a general description of a preferred method for the harvest of porcine reticulocytes and preparation of a reticulocyte control composition having a plurality of levels. However, other methods of harvesting porcine reticulocytes could also be used without departing from the present invention. The red blood cell and white blood cell components for the present invention can be provided from porcine, human, bovine or other mammalian sources. Further, the blood platelet component of the control can be obtained from whole blood taken from animal species that are non-infectious with respect to human hepatitis, ideally animals of the bovine or porcine species. Alternatively, the platelet component of the present invention can be provided by cells that are stabilized to resemble platelets in the analyzer (e.g. small erythrocytes, obtained, for example, from goat, as commercially available from Beckman/Coulter Corp.), or polystyrene beads.

Reticulocytes can be harvested from a number of suitable mammalian sources, including, for example, porcine and bovine sources. As previously described in U.S. Pat. Nos. 5,736,402, 5,858,789 and 5,945,340, porcine blood contains more reticulocytes (i.e., approximately twice as many reticulocytes, as a percentage of total RBCs) than normal human blood. These patents also disclose that porcine reticulocytes can be recovered and stabilized in a manner that renders them useful as a reticulocyte control composition. Porcine reticulocytes appear less mature than normal human reticulocytes and, as such, they provide a substantially homogeneous population of cells that can then be arrested to minimize further development of the cells. The present inventors have found that the relative abundance of reticulocytes, the large volumes of blood that are available, and the strong discrimination against reticulocyte rouleaux formation in the pig can all be used to effectively produce large volumes of an enriched fraction having a high reticulocyte concentration.

One method of harvesting reticulocytes for use in the control involves differential sedimentation of reticulocytes and RBCs as described in detail below. In the first sedimentation step, a platelet-rich supernatant and corresponding sediment fraction that contains reticulocytes and RBCs are formed. The platelet-rich supernatant can be removed and used for other purposes (e.g., the supernatant can be further processed to provide the platelet component of the present invention, as described herein), while the sediment fraction can be resuspended and subjected to a second sedimentation step. The supernatant fraction formed as the result of the second sedimentation step (the "second supernatant fraction") has been found to be particularly rich in reticulocytes.

While not intending to be bound by a particular theory, the present inventors believe the effectiveness of the differential sedimentation method as described above is a result of rouleaux formation of RBCs in a sample. While reticulocytes do not generally form rouleaux either with each other or with mature RBCs, it is believed that, in the initial sedimentation step, reticulocytes are trapped within RBC rouleaux bodies. Such rouleaux formation allows the RBCs and reticulocytes to be readily separated from other components of the blood (e.g., WBCs, platelets, and other components) in an initial sedimentation step. In the second sedimentation step, it appears that the absence of plasma proteins allows the reticulocytes to be easily separated from RBCs. Moreover, it appears that the RBCs and reticulocytes are sufficiently diluted in solution to allow efficient separation of reticulocytes from RBCs. Apparently, the volume of solution and the absence of plasma proteins in the second sedimentation step is sufficient to allow the RBCs to form rouleaux without trapping the reticulocytes and pulling them down into the sediment fraction.

One particular advantage of the methods of the present invention is that the reticulocytes can be recovered in a manner that is compatible with the use of the blood for other purposes, e.g., the recovery of platelets. Porcine blood can be recovered from any suitable source. Preferred procedures for the preparation of platelets involve the recovery of porcine blood from healthy pigs sacrificed the same day.

U.S. Pat. Nos. 4,324,686 and 4,338,564 (both of which are commonly owned by the assignee of the present invention), the disclosures of which are incorporated herein by reference, describe methods for the preparation of compositions and controls containing mammalian platelets. The methods described in these patents are suitable for use in the initial steps of the presently claimed method. As described in these patents, platelets can be prepared from whole blood by first treating the blood to isolate and remove the RBCs; processing the platelets to stabilize them (i.e., to inhibit their surface aggregation with adjacent platelets); harvesting the platelets; and resuspending the stabilized platelets. In a preferred embodiment, the whole blood source should be non-human and non-simian; that is, it should be from a species that is non-infectious with respect to human pathogens. Ideally, the whole blood is taken from bovine or porcine species because such blood is readily available, is susceptible to processing, and does not transmit human pathogens.

In one embodiment of the invention, a first sedimentation step provides a platelet-rich supernatant and a reticulocyte-rich sediment fraction. This can be carried out using a sedimenting solution such as an anticoagulant that facilitates the separation of a red blood cell sediment or pellet, and a platelet-rich plasma supernatant from a whole blood smaple. In this first sedimentation step, RBCs and reticulocytes sediment, and other components of the blood (e.g., WBCs and platelets) remain in the supernatant. In the second sedimentation step, the first sediment is resuspended and allowed to sediment again, separating RBCs from the reticulocytes. As a result of the second sedimentation step, the RBCs sediment, and the reticulocytes are found in the supernatant. The process is described in more detail below.

Newly recovered blood may be added directly to a large carboy containing a suitable amount (e.g., 2.5 liters CCD, as described in the Examples) of the sedimenting solution. While suitable formulation for the preparation of a sedimenting solution is provided below, given the teaching of the present invention those skilled in the art will be able to determine the actual amount of the sedimenting solution that is sufficient to prevent blood clot formation in the blood sample, while at the same time allow differential sedimentation of red blood cells as described below. The sedimenting solution for use in this differential sedimentation preferably includes anticoagulants, (for example, EDTA, heparin), and/or other high molecular weight polysaccharides (e.g., dextran) or polypeptides (e.g., gelatin and other polypeptides). An optimal sedimenting solution includes citric acid, sodium citrate, and dextran, in an aqueous solution.

The mixture of whole blood and sedimenting solution is prepared and allowed to settle at room temperature. After settling, a dense sediment is formed that is dark red in appearance. Above the sediment there is a translucent straw-colored, platelet-rich supernatant. The supernatant is removed, e.g., by aspiration or siphoning, taking care not to disturb the interface.

The present inventors have discovered that reticulocytes can be recovered by processing either the red cell sediment or supernaturant formed in the above sedimentation. In one embodiment, reticulocytes are recovered in the red cell sediment formed during the centrifugation of the above supernatant, the step being necessary to remove platelets. It appears that reticulocytes are suspended in the platelet rich supernatant due to their inability to undergo rouleaux formation. In order to recover the reticulocytes, the platelet-rich plasma supernatant is centrifuged and the resulting sediment is recovered. This sediment is then resuspended in sedimenting solution and Reticulocyte Storage Buffer. In a preferred embodiment, reticulocyte storage buffer is a medium comprising BSA (bovine serum albumin), potassium chloride, tripotassium citrate and dipotassium phosphate. Optimally, the reticulocyte storage buffer includes a eucaryotic protein synthesis inhibitor. Cycloheximide is a particularly preferred inhibitor, since it appears to provide an irreversible stabilizing effect on the porcine reticulocytes. Attempts to induce maturation in porcine reticulocytes after about 15 hours of exposure to Reticulocyte Storage Buffer resulted in reticulocytes that do not lose significant amounts of their stainable RNA over a period of approximately 2 to 4 months of the product life. A more detailed description of this Reticulocyte Storage Medium is included in the Examples.

The resuspended sediment is incubated overnight at room temperature, in order to allow the mature RBCs to settle. This results in a compact cell sediment containing mostly RBCs and an upper supernatant fraction. The supernatant fraction is removed and centrifuged to separate the cells from the medium. The cells are washed several times in Reticulocyte Storage Buffer to remove as many WBCs and platelets as possible, in the process concentrating the reticulocytes to about $1/10$ to about $1/20$ the original volume. The final suspension is passed through a leucodepletion filter (or an equivalent filter) to remove most of the remaining WBCs and any platelet aggregates. Finally, the cells are washed with Reticulocyte Storage Buffer by gentle centrifugation to remove remaining platelets which may have passed through the filter. This process is described in more detail in the Examples.

Alternatively, reticulocytes can be recovered from the red cell sediment formed in the initial sedimentation step, even though reticulocytes are not believed to themselves form rouleaux with mature RBCs. Rather, it appears that the reticulocytes are trapped within or between the rouleaux formed by the RBCs. In order to recover the reticulocytes, the first sediment is resuspended to the original sample volume by adding the sedimenting solution.

The resuspended first sediment is incubated overnight at room temperature, in order to allow the RBCs to settle. This results in a compact cell sediment containing mostly RBCs and an upper supernatant fraction that is darker red in appearance than the first supernatant. The supernatant fraction is removed and centrifuged to separate the cells from the solution. The cells are washed and filtered to concentrate the reticulocytes.

The suspension is analyzed on a hematology analyzer for numbers of reticulocytes. Typical specifications of the reticulocyte fraction, for example, include about 85–95% reticulocytes. The cells are finally harvested by centrifugation and resuspended in Reticulocyte Storage Buffer.

In an optimal embodiment, the Reticulocyte Storage Buffer includes a eucaryotic protein synthesis inhibitor. In a particularly preferred embodiment, the eucaryotic protein synthesis inhibitor is selected from cycloheximide or rifampicin. One of skill in the art would readily understand that other protein synthesis inhibitors could be used without departing from the scope of the present invention. The Reticulocyte Storage Buffer also preferably lacks a carbon or other energy source useful for continued metabolism. In the absence of maturation inhibitors and/or in the presence of an energy source, reticulocytes may continue to develop and thereby lose stainable RNA material, even at lower temperatures.

In one embodiment, the relative maturity of the arrested reticulocytes is manipulated to provide a desired profile. Reticulocytes can be separated based upon relative density (e.g., by centrifugation) to select for the desired maturity level. In this embodiment, reticulocytes may be separated into low and high maturity fractions by density gradient centrifugation using either percoll, ficoll, or arabinogalatan to form the gradient structure. Reticulocytes form bands in the gradient from low to high density which corresponded to immature to mature fractions which could be separated to form secondary stocks. Such separation can be performed at any time during the reticulocyte preparation procedure. In an alternative embodiment, a desired maturity profile can be generated by allowing pools of porcine reticulocytes to mature for various time periods prior to treatment with the Reticulocyte Storage Buffer. The resulting reticulocyte preparation can be separated to form secondary stocks. These stocks of reticulocytes may be mixed in different proportions to prepare final control material exhibiting the desired reticulocyte maturity profile.

In a particularly preferred embodiment, the control solution includes one or more preservatives to prolong shelf life stability. As used herein, the term "preservatives" refers to antimicrobial compounds that do not affect the cells in an adverse way (e.g., by causing hemolysis of RBCs or a change in MCV). For example, fairly young reticulocytes in human blood cell samples were found to be stable after storage for over 2 months at 4° C. in a Reticulocyte Storage Buffer such as exemplified below. Suitable preservatives include, but are not limited to, nalidixic acid, p-hydroxybenzoate methyl ester, p-hydroxybenzoate propyl ester, and penicillin.

In preparing such a whole blood control including reticulocytes, care must be taken so that the addition of reticulocytes does not interfere with measurements of other constituents of the sample (e.g., WBCs and platelets). Parameters such as the mean red cell volume (MCV) and the mean red cell hemoglobin concentration (MCHC) which resemble red cell measurements (including the reticulocyte component) must be carefully monitored to avoid undesirable results. As shown in the Examples, inclusion of cells that simulate reticulocytes and contain a nucleus (e.g., avian red blood cells) may interfere with measurements of other nucleated cells, e.g., the total white cell count, and/or with the entire white cell differential of the control.

A composition of the present invention is preferably provided in the form of an in vitro diagnostic reagent that includes arrested stabilized reticulocytes in combination with RBCs, stabilized mammalian WBCs (or analogs thereof) and platelets (or analogs thereof), all suspended in a plasma-like fluid containing suitable preservatives. Reticulocyte levels between about 0.5% and about 25% can be prepared by judicious combination of reticulocytes (prepared as described herein), with RBCs, WBCs and platelets. A number of suitable methodologies can be used for the preparation of RBCs, WBCs, and platelets. Various analogs that mimic the physical characteristics of the different human blood cell components, but that may be easier to produce, more cost-effective, or provide greater shelf life may be used as substitutes for any one or more of the WBCs and/or platelets.

A suitable matrix which provides the red cells, white cells and platelets to which reticulocytes may be added to form a CBC/WBC differential plus reticulocyte control is CBC-4K™ Hematology Control, available from R&D Systems, Inc., Minneapolis, Minn. Alternatively, processes for the preparation of the formed elements of blood to which reticulocytes can be added are described in U.S. Pat. No. 5,858,790 (Hematology Reference Control and Method of Preparation). Moreover, the platelet component can be provided using the methods described in U.S. Pat. Nos. 4,324,686 and 4,338,564, described above.

A control composition of the present invention can be used according to established laboratory hematology practice to monitor the performance of diagnostic tests. Preferred compositions are composed of stable materials that provide a means of verifying accuracy and precision of reticulocyte counting methods, as well as stabilized components necessary to serve as control material for complete blood count and white cell differential.

Any human blood components used in the preparation of such a composition should be suitably tested in order to ensure that they are negative for all necessary infectious agents or indicators, including hepatitis B surface antigen (HBsAg), hepatitis C virus antibody (anti-HCV), and human immunodeficiency virus antibody (anti-HIV). Since no test available can provide total assurance that specimens of human origin will not transmit infectious disease, health care professionals and lab technicians recognize that particular care should be used with any such composition.

In a preferred embodiment, the present invention is used to prepare a plurality of control levels, as well as appropriate levels of the other complete blood count control constituents. Generally, the reticulocyte fraction of the control ranges from between about 0.5% to about 25% of the total red blood cell count of the control, preferably between about 0.5% to about 15%, and optimally from between about 1% to about 12%. In one embodiment, the present invention is used to prepare a low reticulocyte level control (Level 1), a normal level control (Level 2), and a high level control (Level 3). Examples of preferred quantities for individual components of level 1, level 2, and level 3 controls are given in Table I below.

TABLE I

| Component | Level 1 | Level 2 | Level 3 |
| --- | --- | --- | --- |
| Total RBC (×10$^6$ per µl sample) | 2–3 | 3–4 | 4–6 |
| Reticulocyte (% of total RBC content) | 6–11 | 3–6 | 0.5–3 |
| WBC or WBC analog (×10$^3$ per µl sample) | 2–4 | 7–9 | 16–20 |
| Platelet or platelet analog (×10$^3$ per µl sample) | 40–80 | 220–280 | 400–500 |

The above figures are approximate figures only, and the respective components can be manipulated to provide a control of any desired concentration, so long as the control composition is capable of providing accurate measurements of the individual components.

In a particularly preferred embodiment, the present invention contemplates a CBC/WBC differential control including reticulocytes. The WBC populations in the three controls described in Table I can be further controlled to define specific WBC subpopulations (e.g., neutrophils, lymphocytes, monocytes and eosinophils). Examples of preferred quantities for individual WBC subpopulations of the low, normal and high control levels for such differential controls are given in Table II below.

TABLE II

|  | Percentage of Total WBC Content | | |
| --- | --- | --- | --- |
| WBC Subpopulation | Low | Normal | High |
| Neutrophils | 20–35% | 60–70% | 60–80% |
| Lymphocytes | 45–65% | 20–30% | 15–25% |
| Monocytes | 7–17% | 5–10% | 2–10% |
| Eosinophils | 3–10% | 2–8% | 2–10% |

In another embodiment, the present invention provides a CBC/WBC differential plus reticulocyte control kit. A typical control kit includes separate vials containing reticulocytes ranging between about 0.5% to about 25%, preferably between about 1% to about 12%. A preferred kit, for instance, includes a plurality of concentrations, e.g., 1%, 5%, and 12%. Concentrations over about 25% tend to have little clinical usefulness, since they are rarely encountered in practice. On the other hand, concentrations less than about 0.5% are difficult to determine with both accuracy and precision by conventional detection techniques.

In use, a vial containing the composition of the present invention is typically removed from refrigerated storage and allowed to warm to room temperature. The composition can be mixed by gently rolling the vial between the palms of the hands, and inverting the vial until the cells appear to be completely and uniformly suspended. Care should be taken to avoid undue agitation of the vial, such as by use of a vortex, since agitation can disrupt the cells. The composition can then be incorporated into the analytical procedure of choice in the same manner as a patient sample; for instance with automated methods, the control is analyzed in the manner provided with the operator's manual for the particular instrument. The composition is preferably used within a reasonable time, depending upon the particular method employed (e.g., within about 60 minutes, after warming to room temperature). After removing an aliquot from the vial, the control composition can be re-stored for later use, preferably after carefully wiping the vial rim and cap and returning the capped vial to the refrigerator.

Assay values are typically presented as a mean and a range. The mean is derived from replicate testing by the specific method. Instruments used for automated methods are operated and maintained according to the instrument manufacturer's instructions. The range is an estimate of variation between laboratories and takes into account inherent imprecision of the method, differences in maintenance, operating technique, and equipment. It is generally recommended that each laboratory establish its own laboratory-specific ranges for greater intra laboratory control sensitivity. A composition of the present invention can be used as a control composition in most, if not all, of the most common conventional methods for reticulocyte and complete blood count evaluation, as discussed below.

SYSMEX R™ Series Reticulocyte Counters and SYSMEX XE-2100™:

In 1989, TOA Medical Electronics Co. LTD, Kobe Japan, introduced a benchtop flow cytometer known as the Sysmex R-1000™ Reticulocyte Analyzer. Three years later, an upgraded R-series analyzer, the R-3000™ was released. In these analyzers, the blood sample is aspirated, diluted and stained automatically by auramine O, which carries a positive charge, resulting in an attraction to the negatively charged ribonucleic acid (RNA) and deoxyribonucleic acid (DNA). The samples are hydrodynamically focused and passed through a flow cell. The cell is illuminated by a laser beam at a wavelength of 488 nm. The R-3000™ measures forward fluorescence using a filter to obstruct a shorter wavelength of light and a photomultiplier tube to determine the intensity. The R-1000™ measures side fluorescence using a filter placed at a 90 degree angle to the laser beam. Forward scatter measures the cell size and fluorescence indicates the RNA content of the sample. The fluorescence and scattered light of the individual cells allow these instruments to count the reticulocytes. The instruments analyze about 30,000 cells per sample, determining the reticulocyte count, reticulocyte ratio, and total RBC count. This methodology can analyze far more cells than the manual method, thus increasing the reproducibility and precision. Both instruments use scattergrams divided into platelets, mature RBCs and reticulocyte regions. The reticulocyte region is further divided into three areas: low fluorescence (LF), middle fluorescence (MF), and high fluorescence (HF), and the relative number of cells in these areas can be used to estimate the maturity of the red cell population. A region of very highly fluorescent events counts are not included in the reticulocyte count.

The Sysmex XE-2100™ seeks to integrate the above method with the determination of the CBC/WBC plus WBC differential in a fully automated manner. In this system, part of the sample stream is mixed with a fluorescent dye, and the resulting fluorescence is measured. The remainder of the sample is used to determine the CBC plus WBC differential. This instrument is not yet available in the United States.

BAYER H*3™/ADVIA 120™:

Bayer introduced the H*3™ hematology analyzer in 1993, partly in response to the growing demand for automated reticulocyte counting. The H*3™ is a automated flow cytometer that analyzes reticulocytes in semi-automated fashion by first staining an aliquot of blood with oxazine 750, a blue dye which stains the RNA contained in the cell. The diluted blood sample is then aspirated directly into a flow cell which is illuminated with a helium/neon laser. The reticulocytes are separated from the mature red cell population based on their greater absorbance. The Advia-120™ analyzer introduced in 1998 automates this entire process and reports the reticulocyte measurement as part of the complete sample report.

COULTER STKS™/MAXM™/GENS™:

Coulter Corporation uses their VCS technology (Volume, Conductivity and Scatter), to provide reticulocyte percentages based on new methylene blue staining. Like the H*3™ above, the STKS™ and MAXM™ procedures are semi-automated. First, an aliquot of sample is diluted into a new methylene blue solution and incubated at room temperature for between 5 and 60 minutes. Next, a small volume of the stained sample is diluted with an acid solution that clears the cellular hemoglobin but preserves the RNA-new methylene blue complex. The sample is then introduced directly to the flow cell where reticulocytes are discriminated from mature cells on the basis of their light scatter. The GENS™ uses the same method to enumerate reticulocytes, but performs the analysis as part of the complete blood count without the need for prestaining.

ABBOTT CELL DYN 4000™:

The Abbott Cell Dyn 4000™, introduced in 1995, represents the first fully automated hematology analyzer to offer reticulocytes as part of its analytic menu. Reticulocyte counts and an estimate of reticulocyte maturity may be obtained along with the CBC plus differential without any obligate prework of the sample. On demand, the analyzer stains a portion of the diluted blood sample with a proprietary fluorescent dye. The stained sample is illuminated with an argon laser at 488 nm and the fluorescence intensity and forward light scatter of the red cell population is measured. Reticulocytes are separated from red cells based on their fluorescence. Since this determination is based on a sensitive fluorescence measurement, it represents the most robust of any of the hematology analyzer-based methods yet mentioned.

ABX PENTRA 120™:

The ABX Pentra 120™ is another fully automated hematology analyzer to offer reticulocyte counting. On demand, the analyzer stains a portion of the blood sample with thiazole orange dye (available from Becton Dickinson in pre-diluted form under product name Retic-COUNT™). Staining with thiazole orange increases with time and temperature, and those skilled in the art will appreciate the manner in which these parameters can be standardized. The stained sample is illuminated with an argon laser at 488 nm and the fluorescence intensity and forward light scatter of the red cell population is measured. Reticulocytes are separated from red cells based on their fluorescence.

In summary, control compositions of the present invention can be formulated to perform well in each of the automated systems described above, as well as other suitable automated systems, using the methodologies suggested by the manufacturers. In particular, the present invention provides an improved hematology control that more accurately resembles a patient sample, in that it allows the instrument to measure the CBC/WBC plus differential, plus reticulocyte levels in a unitary sample. The present invention thus provides an improved combination of properties such as the resulting control composition provides an optimal combination of such properties as true reticulocyte appearance and stain characteristics, stability, uniformity and wide utility as a control with most, if not all, presently available assay techniques. Additionally, the present invention provides a unitary control that more closely resembles a patient sample and allows measurement of reticulocyte levels and relative maturity of reticulocytes.

The invention will be further described with reference to the following non-limiting examples.

EXAMPLES

Reagent Preparation

The following reagents were prepared in advance:

CCD Solution:

The following ingredients were combined and made to 60 liters with deionized water: citric acid (142.63 g), sodium citrate (3210 g), Dextran (3600 g, Sigma No. D-4876, molecular weight range 150 kD to 180 kD). The pH of the solution was adjusted to about 7.2 with sodium hydroxide.

| Reticulocyte Storage Buffer: | | |
|---|---|---|
| Component | Units | Quantity per Liter |
| Albumin, Bovine (30%) | mL | 100 |
| Chloride, potassium | g | 4 |
| Citrate, tripotassium | g | 3 |
| Cycloheximide | g | 0.5 |
| Phosphate, dipotassium | g | 5 |
| Methyl paraben | g | 0.5 |
| Propyl paraben | g | 0.5 |
| Nalidixic acid | g | 0.5 |
| Penicillin, Sodium | g | 0.5 |

The ingredients were combined and the pH of the solution was adjusted to 7.5 (+/−1), with an osmolality of approximately 340 mOsm/liter (+/−15 m mOsm/liter). After the ingredients were added to the solution, sterile filtration was accomplished by peristaltic pumping through a terminal 0.2 micron minicapsule filter of 500 square cm surface area.

Example 1

Porcine reticulocytes were harvested and prepared as a control composition in the following manner:

1. Recovery of Porcine Blood.

Porcine blood was collected from freshly sacrificed pigs and added to fill 20 liter carboys containing 2.5 liters of CCD solution (prepared as described above).

2. First Sedimentation Step.

The blood/CCD mixture was allowed to continue to settle, for a total incubation time of approximately three (3) hours. Upon settling, a dense sediment was formed that was dark red in appearance. Above the sediment there was a sharp interface between the sediment and the translucent straw-colored, platelet-rich supernatant.

3. Separation of First Supernatant.

The supernatant (approximately 12 liters of the original 20 liters) was removed by aspiration, taking care not to disturb the interface between plasma and cells.

4. Separation of Platelet Rich Plasma from Reticulocyte Rich Sediment.

To recover reticulocyte rich sediment, the platelet-rich plasma above was centrifuged for three minutes at 4500 RPM in a GSA rotor (RC5 Sorvall centrifuge). The supernatant was removed and the sediments were recovered and combined into a common pool of concentrated cells.

5. Separation of Reticulocyte Rich Supernatant.

In order to recover the reticulocytes, about 8 liters of this pooled sediment was resuspended in about 2 liters of CCD and 10 liters of Reticulocyte Storage Buffer. The resuspended sediment was incubated overnight (e.g., about 15 hours) at room temperature, in order to allow the mature RBCs to settle. The supernatant fraction was removed and centrifuged at 4500 RPM in a GSA rotor (RC5 Sorvall centrifuge) for 15 minutes to separate the cells from the medium. The cells were washed several times in Reticulocyte Storage Buffer to remove as many WBCs and platelets as possible, in the process concentrating the reticulocytes to achieve a total cell count of between $0.4 \times 10^6$ cells per microliter and $0.6 \times 10^6$ cells per microliter. The final suspension was passed through a leukocyte-depletion filter (Pall, RCXL2 or equivalent) to remove most of the remaining WBCs. Finally, the cells were washed with Reticulocyte Storage Buffer by centrifugation at 4500 RPM in a GSA rotor (RC5 Sorvall centrifuge) for 3 minutes to remove remaining platelets which may have passed through the leukocyte-depletion filter.

The final pellet was resuspended in Reticulocyte Storage Buffer to achieve a concentration of $3.8 \times 10^6$ cells per microliter to $4.2 \times 10^6$ cells per microliter. The suspension was analyzed on a hematology analyzer and were found to contain about 85% to about 95% reticulocytes. The concentrate was refrigerated at 2–8° C. pending further use.

Example 2

The final assayed fractions prepared in Example 1 were used to prepare various control levels of reticulocytes (1%, 5%, and 12%) for use in a control kit. To provide control compositions having porcine reticulocytes in a complete blood count base, suitable mixtures were made of the suspension formed in step 5 above.

Three levels of red blood cells, white blood cells, and platelets were added as appropriate to allow for "tri-level" controls of these constituents as well. To prepare three levels of control, red cells were selected on the basis of volume and diluted to the appropriate concentrations shown in Table I. The cells were then combined with chemically stabilized white cells and platelets. Therefore, based on a calculation of required volume of white cell stock suspension (typically containing one million white cells per microliter), this volume was added to the red cell suspension, mixed completely, and analyzed on the cell counter of interest to confirm correctly targeted WBC count.

Similarly, based upon a calculation of required volume of platelet stock suspension, (typically containing ten million platelets per microliter), this volume was added to the control cell suspension, mixed completely, and analyzed on the cell counter of interest to confirm correctly targeted cell count. After final adjustments and analysis to confirm correct targets, the control was refrigerated pending subdivision of the formulation into final packaging.

The various control levels prepared above were tested in four diagnostic systems as directed in the appropriate operating instructions. The results can be seen in Tables III and IV below. The data show that the measured WBC, RBC, reticulocytes and platelets between the various techniques are quite close. The data indicate that the control preparations of the present invention have wide applicability in most, if not all, presently available instruments and techniques. Moreover, the present control provides accurate, reproducible results for all components measured. These values were consistent for not only each level of control, but also across the various instruments used.

TABLE III

|  | Bayer H*3 ™ Recoveries | | | Coulter STKS ™ Recoveries | | |
| --- | --- | --- | --- | --- | --- | --- |
|  | Level 1 | Level 2 | Level 3 | Level 1 | Level 2 | Level 3 |
| Total RBC (×10⁶ per μl of sample) | 2.38 | 3.90 | 5.42 | 2.35 | 3.88 | 5.36 |
| Reticulocyte (% of total RBC content) | 10.2 | 4.8 | 1.2 | 8.5 | 4.1 | 0.76 |
| WBC (×10³ per μl of sample) | 2.6 | 8.1 | 18.1 | 2.5 | 8.2 | 18.3 |
| Platelets (×10³ per μl of sample) | 44 | 245 | 448 | 48 | 252 | 456 |
| MCV (fl) | 70.4 | 81.5 | 90.1 | 72.2 | 83.5 | 91.1 |

TABLE IV

|  | Abbott CD-4000 ™ Recoveries | | | ABX Pentra ™ Recoveries | | |
| --- | --- | --- | --- | --- | --- | --- |
|  | Level 1 | Level 2 | Level 3 | Level 1 | Level 2 | Level 3 |
| Total RBC (×10⁶ per μl of sample) | 2.26 | 4.01 | 5.45 | 2.28 | 3.94 | 5.32 |
| Reticulocyte (% of total RBC content) | 10.8 | 5.2 | 1.6 | 10.5 | 4.9 | 1.1 |
| WBC (×10³ per μl of sample) | 2.3 | 7.9 | 17.8 | 2.4 | 7.8 | 18.1 |
| Platelets (×10³ per μl of sample) | 46 | 238 | 432 | 47 | 247 | 461 |
| MCV (fl) | 69.8 | 80.4 | 89.3 | 71.9 | 82.4 | 90.8 |

Example 3

Figure 2:
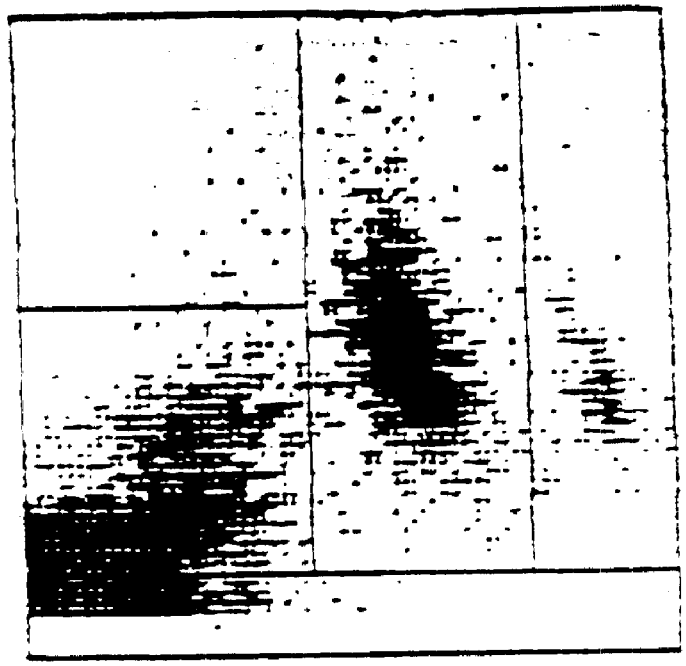
FIG. 2 is a WBC cytogram of a composition including avian RBCs combined with R&D Systems CBC-5D™ Hematology Control, run on a Coulter STKS™ light scatter based on analyzer.

A high level control (Level 3) containing a complete blood count base and reticulocyte component was prepared as follows. Avian blood was collected from sacrificed chickens, and the RBCs were isolated using standard technique. The recovered avian RBCs were then combined as a reticulocyte analog with R&D Systems 5-part differential control (commercially available under the product name CBC-5D™) to represent approximately 10% of the total RBCs of the solution. The resulting composition was mixed completely and analyzed on a Coulter STKS™ cell counter as directed in the appropriate operating instructions provided by the manufacturer. The results of the CBC/WBC differential plus reticulocyte analog composition can be seen in FIGS. 1 and 2, which are cytograms of the stand-alone CBC-5D™ control (FIG. 1), and CBC-5D™ plus reticulocyte analog control (FIG. 2). The data from FIGS. 1 and 2 are summarized in Table V.

The results show that the addition of avian RBCs to a complete blood count base yields an unacceptable CBC/WBC differential plus reticulocyte control. Specifically, the addition of nucleated cells as an analog for the reticulocyte component of such a control interferes not only with the measurement of total WBCs of the control, but also interferes with the measurements of the differential portion of the control (i.e., the subpopulations of WBCs). FIG. 1 shows a cytogram of the CBC-5D™ control run on the Coulter STKS™, showing proper numerical reports for the WBC differential portion of the control. FIG. 2 shows a cytogram of the CBC-5D™ plus avian RBCs run on the Coulter STKS™. As seen in FIG. 2, lysis of the RBCs for the differential determination leaves avian RBC nuclei that interfere with the differential presentation. This in turn causes a "vote out" (i.e., failure to report) of the total WBC count and the absolute count of each of the parts of the differential and incorrect percentages of the differential. As shown in Table V, absolute counts of the total WBC content, as well as WBC subpopulations, were unattainable for the CBC plus reticulocyte analog.

TABLE V

|  | CBC - 5D control | CBC - 5D control plus reticulocyte analog |
| --- | --- | --- |
| Total RBC (×10⁶ per μl of sample) | 5.54 | 5.46 |
| Reticulocyte (% of total RBC content) | — | 10% |
| Total WBC (×10³ per μl of sample) | 21.9 | *** |
| Neutrophils (% of the total WBC content) | 68.4 | 29.8 |
| Lymphocytes (% of the total WBC content) | 20.6 | 65.4 |
| Monocytes (% of the total WBC content) | 0.8 | 0.5 |
| Eosinophils (% of the total WBC content) | 9.6 | 4.3 |
| Basophils (% of the total WBC content) | 0.6 | 0.0 |
| Neutrophils (×10³/μl of sample) | 15.0 | *** |
| Lymphocytes (×10³/μl of sample) | 4.5 | *** |
| Monocytes (×10³/μl of sample) | 0.2 | *** |

TABLE V-continued

| | CBC - 5D control | CBC - 5D control plus reticulocyte analog |
|---|---|---|
| Eosinophils (×10³/μl of sample) | 2.1 | *** |
| Basophils (×10³/μl of sample) | 0.1 | *** |

*** indicates a vote out.

While a preferred embodiment of the present invention has been described, it should be understood that various changes, adaptations and modifications may be made therein without departing from the spirit of the invention and the scope of the appended claims.

I claim:

1. A control composition comprising a predetermined concentration of stabilized reticulocytes, and a complete blood count base including mature erythrocytes, stabilized white cells or analogs thereof, and stabilized platelets or analogs thereof, wherein the reticulocytes are maturation-arrested to provide a desired maturation profile.

2. A composition according to claim 1 wherein maturation of the reticulocytes is arrested with a reticulocyte storage buffer.

3. A composition according to claim 2 wherein the reticulocyte storage buffer includes cycloheximide.

4. A composition according to claim 2 wherein the reticulocyte storage buffer includes rifampicin.

5. A composition according to claim 2 wherein the reticulocyte storage buffer lacks an energy source.

6. A composition according to claim 1 further including one or more preservatives.

7. A ready-to-use kit comprising a plurality of control compositions wherein at least one of the control compositions include a predetermined concentration of reticulocytes, mature red blood cells, stabilized white blood cells or analogs thereof, and stabilized platelets or analogs thereof, wherein the reticulocytes are maturation-arrested to provide a desired maturation profile.

8. A ready-to-use kit according to claim 7 wherein the reticulocytes are provided at concentrations from about 0.5% to about 15% of the total red cell count of the control composition.

9. A ready-to-use kit according to claim 8 wherein the reticulocytes are provided at concentrations from about 1% to about 12% of the total red cell count of the control composition.

10. A method of preparing a control composition, the method comprising the steps of: (1) harvesting an enriched population of porcine reticulocytes; (2) treating the reticulocytes with a suitable medium to arrest further maturation; (3) stabilizing the harvested, arrested reticulocytes; and (4) preparing a control composition comprising a predetermined concentration of stabilized, maturation-arrested reticulocytes, red blood cells, white blood cells or analogs thereof, and platelets or analogs thereof.

11. A method according to claim 10 further including the step of generating a maturity profile of the reticulocytes.

12. A method according to claim 10 wherein maturation is arrested by treating the reticulocytes with a reticulocyte storage medium.

13. A method according to claim 12 wherein the reticulocyte storage medium includes cycloheximide.

14. A method according to claim 12 wherein the reticulocyte storage medium includes rifampicin.

15. A control composition comprising a predetermined concentration of a reticulocyte component, and a complete blood count base including mature erythrocytes, stabilized white cells or analogs thereof, and stabilized platelets or analogs thereof and wherein the reticulocyte component is provided at concentrations from about 0.5% to about 25% of the total red blood cell count, wherein the reticulocytes are maturation-arrested to provide a desired maturation profile.

16. A control composition comprising a predetermined concentration of a reticulocyte component, and a complete blood count base including mature erythrocytes, stabilized white cells or analogs thereof, and stabilized platelets or analogs thereof and wherein the reticulocyte component is provided at concentrations from about 0.5% to about 15% of the total red blood cell count, wherein the reticulocytes are maturation-arrested to provide a desired maturation profile.

17. A control composition comprising a predetermined concentration of a reticulocyte component, and a complete blood count base including mature erythrocytes, stabilized white cells or analogs thereof, and stabilized platelets or analogs thereof and wherein the reticulocyte component is provided at concentrations from about 1% to about 12% of the total red blood cell count, wherein the reticulocytes are maturation-arrested to provide a desired maturation profile.

* * * * *